United States Patent [19]

Nishio et al.

[11] Patent Number: 5,155,231
[45] Date of Patent: Oct. 13, 1992

[54] PROCESS FOR PREPARATION OF 3,4,5,6-TETRAHYDROPHTHALIMIDE

[75] Inventors: Kenji Nishio, Ootsu; Shoji Tani, Nishinomiya, both of Japan

[73] Assignee: New Japan Chemical Co., Ltd, Kyoto, Japan

[21] Appl. No.: 604,504

[22] Filed: Oct. 29, 1990

[51] Int. Cl.$^5$ .......................................... C07D 209/49
[52] U.S. Cl. .................................................. 548/480
[58] Field of Search .......................................... 548/480

[56] References Cited

PUBLICATIONS

Ficken et al., "Conjugated Macrocycles", J. Chem. Soc. (1952) 4846-4854.
*Chemical Abstracts* vol. 96 Abstract No. 35083p (1982).
Chemical Abstracts vol. 71 Abstract No: 38400j (1969).

*Primary Examiner*—Joseph Paul Brust
*Assistant Examiner*—Jacqueline Haley
*Attorney, Agent, or Firm*—Larson and Taylor

[57] ABSTRACT

Disclosed is a process for preparing 3,4,5,6-tetrahydrophthalimide comprising the steps of:

(i) reacting a crude 3,4,5,6-tetrahydrophthalic anhydride containing as impurities at least one carboxylic anhydride (A) selected from the group consisting of phthalic anhydride, hexahydrophthalic anhydride and structural isomers of 3,4,5,6-tetrahydrophtalic anhydride with an alcohol for conversion of substantially all the carboxylic anhydride (A) into the monoester thereof to obtain a reaction mixture containing the monoester, 3,4,5,6-tetrahydrophthalic anhydride, and if any, a monoester of 3,4,5,6-tetrahydrophthalic anhydride, and (ii) adding ammonia to the reaction mixture to subject the 3,4,5,6-tetrahydrophthalic anhydride, and if any, the monoester thereof to a reaction for conversion into 3,4,5,6-tetrahydrophthalimide.

19 Claims, No Drawings

PROCESS FOR PREPARATION OF 3,4,5,6-TETRAHYDROPHTHALIMIDE

BACKGROUND OF THE INVENTION

1. Field of the Invention

The present invention relates to a commercially advantageous process for preparing 3,4,5,6-tetrahydrophthalimide (hereinafter referred to as "$\Delta^1$-THPI").

2. Prior Art $\Delta^1$-THPI is an industrial material useful as the intermediate for preparation of insecticides, herbicides or like agricultural chemicals.

Conventional processes for preparing $\Delta^1$-THPI include the following processes.

(1) A process comprising heating 3,4,5,6-tetrahydrophthalic anhydride (hereinafter referred to as "$\Delta^1$-THPA") and urea to a temperature of 155° to 160° C. and recrystallizing the obtained reaction product from benzene for separation (J. Chem. Soc., 4846, (1952)):

(2) A process comprising reacting $\Delta^1$-THPA with aqueous ammonia at a temperature of 110° to 160° C. (Khim. Farm. Zh., [3], 28 (1969)):

(3) A process comprising reacting $\Delta^1$-THPA with an ammonia gas at a temperature of 145° to 152° C. (U.S.S.R. Inventor's Certificate No.859,363).

However, the foregoing processes require the use of a high-purity $\Delta^1$-THPA as the starting material in order to obtain a high-purity $\Delta^1$-THPI in high yields.

For the production of $\Delta^1$-THPA serving as the starting material, we have proposed methods in which 1,2,3,6-tetrahydrophthalic anhydride (hereinafter referred to as "$\Delta^4$-THPA") is isomerized (Japanese Examined Patent Publications No. 54144/1983 and No.54148/1983).

These methods for preparing $\Delta^1$-THPA, although commercially advantageous, give a reaction product containing about 1 to about 10% of carboxylic anhydrides (hereinafter referred to as "contaminating phthalic anhydrides") such as hexahydrophthalic anhydride, phthalic anhydride and $\Delta^4$-THPA (i.e. 1,2,3,6-tetrahydrophthalic anhydride) or like structural isomer of $\Delta^1$-THPA.

When ammonia is acted on such starting material comprising $\Delta^1$-THPA as the main component and the contaminating phthalic anhydrides in the conventional manner, not only the $\Delta^1$-THPA but also the contaminating phthalic anhydrides are converted into the corresponding imides. These imides can not be easily separated from one another and thus necessitate a separation procedure for isolation. Consequently a high-purity $\Delta^1$-THPI can not be produced in high yields.

SUMMARY OF THE INVENTION

It is an object of the present invention to provide a commercially advantageous process for preparing a high-purity $\Delta^1$-THPI.

According to the present invention, there is provided a process for preparing 3,4,5,6-tetrahydrophthalimide, the process comprising the steps of:

(i) reacting a crude 3,4,5,6-tetrahydrophthalic anhydride containing as impurities at least one carboxylic anhydride (A) selected from the group consisting of phthalic anhydride, hexahydrophthalic anhydride and structural isomers of 3,4,5,6-tetrahydrophthalic anhydride with an alcohol represented by the formula $$R(OH)_n \qquad (I)$$

wherein R is an alkyl group having 1 to 22 carbon atoms, an alkenyl group having 1 to 22 carbon atoms, an aryl group, an aralkyl group, an alkoxyalkyl group or an alicyclic hydrocarbon group, and n is an integer of 1 to 3 for conversion of substantially all the carboxylic anhydride (A) into a monoester thereof to obtain a reaction mixture containing the foregoing monoester, 3,4,5,6-tetrahyrophthalic anhydride, and if any, a monoester thereof, and (ii) adding ammonia to the reaction mixture obtained in the step (i) to subject the 3,4,5,6-tetrahydrophthalic anhydride and if any, the monoester thereof to a reaction for conversion into 3,4,5,6-tetrahydrophthalimide.

DETAILED DESCRIPTION OF THE INVENTION

We conducted extensive research to develop a commercially advantageous process for preparing $\Delta^1$-THPI, the process being capable of producing a high-purity $\Delta^1$-THPI in a high yield without use of a purified $\Delta^1$-THPA as the starting material. Our research revealed the following.

(I) In the reaction with ammonia for conversion into imides, the monoesters of the contaminating phthalic anhydrides are more stable than $\Delta^1$-THPA or monoesters thereof and are not easily convertible into imides, whereas $\Delta^1$-THPA per se or the monoester thereof is easily convertible into imide.

(II) Therefore, even if a crude $\Delta^1$-THPA containing the contaminating phthalic anhydrides is used as the starting material, only $\Delta^1$-THPA (and a monoester thereof, if any) of the crude $\Delta^1$-THPA is selectively converted into imide, provided that before the conversion of the crude $\Delta^1$-THPA into imide, the contaminating phthalic anhydrides are esterified into monoesters thereof which are difficult to change into imides.

(III) When a specific hydrocarbon inert to the starting material and $\Delta^1$-THPI is used as the reaction medium, the obtained $\Delta^1$-THPI can be more readily separated from the monoesters of the contaminating phthalic anhydrides without resort to recrystallization or like special purification procedure, and a high-purity $\Delta^1$-THPI can be produced in high yields.

The present invention has been accomplished based on these novel findings.

The amount of the contaminating phthalic anhydrides to be acceptable in the invention is not specifically limited, but is typically about 1 to about 20% by weight, preferably about 3 to about 15% by weight from consideration of commercially beneficial composition.

The kind of the alcohol represented by the formula (I) is not specifically limited insofar as the alcohol, when reacted with the contaminating phthalic anhydrides, can form the corresponding monoester which can retain the monoester structure during the reaction for conversion into an imide.

Given below are examples of groups represented by R in the formula (I). Examples of the aryl group are phenyl, substituted phenyl, particularly phenyl substituted with one or two methyl groups, etc.; examples of the aralkyl group are phenyl-$C_1$-$C_6$ alkyl such as benzyl, phenethyl, etc.; and examples of the alicyclic hydrocarbon group are cycloalkyl having 6 to 10 carbon atoms, such as cyclohexyl, decahydronaphthyl, etc. Examples of alkoxyalkyl groups are $C_1$-$C_{22}$ alkoxy-$C_2$-$C_3$ alkyl groups such as methyloxyethyl, ethyloxyethyl, methyloxypropyl, ethyloxypropyl, etc. Among the alcohols of the formula (I) wherein n is 2, preferred are alkylene glycols or cycloalkylene glycols represented by the formula

$$HO-R'-OH \quad (II)$$

wherein R' is an alkylene group having 2 to 10 carbon atoms or an alicyclic hydrocarbon group.

The alcohols of the formula (I) are usable singly, or at least two of them can be used in mixture.

The alcohols of the formula (I) wherein n is 1 include, for example:

(A) branched- or straight-chain aliphatic saturated or unsaturated alcohols having 1 to 22 carbon atoms, such as alcohols wherein R in the formula (I) is methyl, ethyl, propyl, n-butyl, isobutyl, amyl, hexyl, heptyl, n-octyl, 2-ethylhexyl, isooctyl, isononyl, n-decyl, isodecyl, undecyl, dodecyl, tridecyl, myristyl, cetyl, stearyl, behenyl, allyl, oleyl or the like; and adducts of each of these alcohols with $C_2$-$C_3$ alkylene oxide such as ethylene glycol monomethyl ether, ethylene glycol monoethyl ether, etc.

(B) aralkyl alcohols such as benzyl alcohol, phenethyl alcohol, etc.; and (C) alicyclic alcohols such as cyclohexyl alcohol, decahydronaphthol, etc.

Preferred alcohols of the formula (I) wherein n is 2 or 3 are polyhydric alcohols such as ethylene glycol, propylene glycol, glycerin and adducts thereof with $C_2$-$C_3$ alkylene oxide, e.g. diethylene glycol.

Desirable as the alcohols of the formula (I) are those having a boiling point of not lower than 120° C., preferably about 120° to about 180° C., in view of the progress of the reaction for conversion into imides.

The alcohol of the formula (I) is used in an amount effective to convert the contaminating phthalic anhydrides into their monoesters, more specifically, e.g. about 0.1 to about 20 moles, preferably, from consideration of industrial aspect, about 0.5 to about 10 moles, per mole of the crude $\Delta^1$-THPA (in terms of the mean molecular weight as calculated from the neutralization value, the same hereinafter).

When the crude $\Delta^1$-THPA is heated to about 60 to about 140° C. in the presence of the alcohol, preferably in an atmosphere of an inert gas such as nitrogen gas or the like, at least the contaminating phthalic anhydrides are converted to the corresponding monoesters.

When required, the esterification reaction for production of the monoesters may be conducted using as a solvent the hydrocarbon of the type to be used in the reaction for conversion into imides to be described later.

In the foregoing esterification reaction, the monoesterification of the contaminating phthalic anhydrides predominates and substantially the whole of the contaminating phthalic anhydrides are converted to the monoesters, whereas $\Delta^1$-THPA may be converted to its monoester or left unchanged, depending on the amount of the alcohol of the formula (I) used.

The foregoing monoesterification reaction is continued until practically the entire amount of the contaminating phthalic anhydrides in the reaction mixture is esterified into their monoesters. The esterification reaction time is usually about 0.1 to about 2 hours.

The subsequent reaction for conversion into the desired 3,4,5,6-tetrahydrophthalimide (hereinafter referred to as "imide-forming reaction") is conducted by adding ammonia to the reaction mixture of the above esterification reaction.

The imide-forming reaction subsequent to the esterification can be performed without use of a solvent especially when an excess of the alcohol of the formula (I) is used in the esterification. However, the imide-forming reaction efficiently proceeds when the reactants are heated with stirring in a specific hydrocarbon solvent which is inert to the reactants and $\Delta^1$-THPI while gradually adding ammonia.

Examples of preferred hydrocarbons are those having 6 to 16 carbon atoms and include aliphatic hydrocarbons, alicyclic hydrocarbons and aromatic hydrocarbons. These hydrocarbons are usable singly, or at least two of them can be used in mixture.

More specific examples of the hydrocarbon are hexane, heptane, octane, decane, dodecane, cyclohexane, decalin, tetralin, toluene, xylene, mixed hydrocarbons produced in petroleum refining, etc. Among them, preferred are the hydrocarbons having a boiling point of not lower than about 140° C., particularly about 140° C. to about 255° C. (under atmospheric pressure), from the view point of the rate of imide-forming reaction. More preferred are dodecane, decalin, and paraffin-naphthene hydrocarbon mixture having a boiling point of about 140° C. to about 255° C.

The amount of the reaction solvent to be used in the imide-forming reaction is not specifically limited insofar as the desired imide-forming reaction proceeds. The total amount of the hydrocarbon and the alcohol of the formula (I) is usually about 25 to about 250% by weight, preferably about 50 to about 200% by weight, based on the crude $\Delta^1$-THPA.

While ammonia to be used in the imide-forming reaction may be used either in the form of a gas or an aqueous solution, an aqueous ammonia solution is easy to handle and is commercially preferable.

The aqueous ammonia solution is used in a concentration of about 10 to about 35% by weight, preferably about 20 to about 30% by weight.

The amount of the ammonia to be used is about 1.01 to about 2.5 moles, preferably about 1.05 to about 2.2 moles, per mole of the crude $\Delta^1$-THPA. The addition of more ammonia does not produce a significant difference in the effect.

For the production of $\Delta^1$-THPI in high yields, it is desirable to add an aqueous ammonia solution in small amounts, rather than adding the total amount at one time, during the reaction. The ammonia solution may be gradually added. For example, the ammonia solution is added in small amounts continuously from the start of the reaction until the completion thereof such that the total amount of ammonia added will become the above-specified amount.

The reaction temperature is about 100° to about 160° C., preferably about 120° to about 140° C.

The imide-forming reaction is effected at atmospheric pressure, or under reduced pressure or increased pressure insofar as the water formed by the reaction can be distilled off due to vapor-liquid equilibrium or in the form of an azeotropic mixture.

The imide-forming reaction is usually completed in about 2 to about 10 hours.

The imide-forming reaction is carried out preferably in an atmosphere of nitrogen gas or like inert gas.

In the imide-forming reaction, the monoesters of the contaminating phthalic anhydrides produced by the esterification remain without change to imides, while substantially the whole of the $\Delta^1$-THPA and if any, a monoester thereof are easily converted into the desired $\Delta^1$-THPI.

The process for preparing $\Delta^1$-THPI according to the invention can be carried out either batchwise or continuously.

The thus obtained reaction mixture is cooled, whereby the desired product is precipitated as crystals. A high-purity $\Delta^1$-THPI can be obtained merely by separating the crystals by conventional separation method such as filtration and drying the crystals.

EXAMPLES

The present invention will be described below in more detail with reference to the following examples and comparative example.

EXAMPLE 1

A 1-liter four-necked flask equipped with a stirrer, a decanter with a condenser, a thermometer, a nitrogen inlet tube and an ammonia water-feeding unit was charged with 152 g of crude $\Delta^1$-THPA, 200 ml of 2-ethylhexanol (boiling point of 184° C., specific gravity of 0.834 [20° C.]) and 200 ml of a paraffin-naphthene hydrocarbon mixture (tradename "ExxsoL D40", product of Exxon Chemicals, boiling point of 163° to 194° C., specific gravity of 0.770 [15° C.]). The crude $\Delta^1$-THPA had the following composition (as determined by GLC).

| | |
|---|---|
| $\Delta^1$-THPA | 90% by weight |
| Hexahydrophthalic anhydride | 3% by weight |
| Phthalic anhydride | 1% by weight |
| Structural isomer of $\Delta^1$-THPA | 2% by weight |
| Others | 4% by weight |

The mixture in the flask was heated with stirring for 30 minutes to dissolve the crude $\Delta^1$-THPA in the solvent, thereby conducting monoesterification reaction.

Thereafter, 121 g (2.0 moles) of 28 wt. % aqueous ammonia solution was gradually added to the reaction mixture obtained above at 120° C. over a period of 3.5 hours while distilling off the formed water due to vapor-liquid equilibrium or in the form of an azeotropic mixture. The distillate was separated into two layers using a decanter and the aqueous layer was withdrawn from the reaction system. Thus, imide-forming reaction was conducted and $\Delta^1$-THPA and the monoesters thereof in the reaction system were converted into $\Delta^1$-THPI.

After the reaction, the reaction mixture obtained was cooled, and the crystals precipitated were filtered and dried, giving $\Delta^1$-THPI having a purity of 99.9% in a yield of 96%. Here, the purity of the product was determined by gas chromatography and the yield is based on the amount of $\Delta^1$-THPA contained in the crude $\Delta^1$-THPA. The same applies to the purity and yield in each of the following examples and comparative example.

EXAMPLE 2

The same procedure as in Example 1 was repeated except that 200 ml of isononyl alcohol (boiling point of 198° to 205° C., specific gravity of 0.834 [20° C.]) was used as the alcohol and that 200 ml of decalin (boiling point of 196° C., specific gravity of 0.897 [20° C.]) was used as the reaction medium and that the reaction was conducted at 130° C., giving $\Delta^1$-THPI. This desired product had a purity of 99.8% and was obtained in a yield of 95%.

EXAMPLE 3

The same procedure as in Example 1 was repeated except that 50 ml of n-butyl alcohol (boiling point of 117° C., specific gravity of 0.810 [20° C.]) was used as the alcohol and that 250 ml of the paraffin-naphthene hydrocarbon mixture was used as the reaction medium, giving $\Delta^1$-THPI. This desired product had a purity of 99.7% and was obtained in a yield of 95%.

EXAMPLE 4

The same procedure as in Example 1 was repeated except that 200 ml of decyl alcohol (boiling point of 232° C., specific gravity of 0.830 [20° C.]) was used as the alcohol and that 200 ml of dodecane (boiling point of 214° C., specific gravity of 0.751 [20° C.]) was used as the reaction medium, giving $\Delta^1$-THPI. This desired product had a purity of 99.8% and was obtained in a yield of 96%.

EXAMPLE 5

The same procedure as in Example 1 was repeated except that 100 ml of propylene glycol (boiling point of 187° C., specific gravity of 1.038 [20° C.]) was used as the alcohol and that 300 ml of the paraffin-naphthene hydrocarbon mixture was used as the reaction medium, giving $\Delta^1$-THPI. This desired product had a purity of 99.9% and was obtained in a yield of 96%.

EXAMPLE 6

The same procedure as in Example 1 was repeated except that the paraffin-naphthene hydrocarbon mixture was not used and that 300 ml of 2-ethylhexanol was used, giving $\Delta^1$-THPI. This desired product had a purity of 99.8% and was produced in a yield of 86%.

EXAMPLE 7

The same procedure as in Example 1 was repeated with the exception of using different crude $\Delta^1$-THPA having the following composition (as determined by GLC), giving $\Delta^1$-THPI. This desired product had a purity of 99.9% and was prepared in a yield of 96%.

| | |
|---|---|
| $\Delta^1$-THPA | 87% by weight |
| Hexahydrophthalic anhydride | 6% by weight |
| Phthalic anhydride | 3% by weight |
| Structural isomers of $\Delta^1$THPA | 1% by weight |
| Others | 3% by weight |

COMPARATIVE EXAMPLE 1

The same procedure as in Example 1 was repeated except that alcohols were not used and that 400 ml of the paraffin-naphthene hydrocarbon mixture was used as the reaction medium, giving $\Delta^1$-THPI. This product had a purity of 92.1% and was obtained in a yield of 108%. This means that the product contains impurities such as free acids of the contaminating phthalic anhydrides, ammonium salts thereof, etc.

As seen from the foregoing Examples and Comparative Example, the process of the present invention can provide $\Delta^1$-THPI of high purity in a high yield with ease without necessitating any means for purification of reactants and reaction products.

We claim:

1. A process for preparing 3,4,5,6-tetrahydrophthalimide, comprising the steps of:
   (i) reacting a crude 3,4,5,6-tetrahydrophthalic anhydride containing as impurities at least one carboxylic anhydride (A) selected from the group consisting of phthalic anhydride, hexahydrophthalic anhydride and structural isomers of 3,4,5,6-tetrahydrophthalic anhydride, with an alcohol represented by the formula $$R(OH)_n \qquad (I)$$

wherein R is selected from the group consisting of an alkyl group having 1 to 22 carbon atoms, an alkenyl group having 1 to 22 carbon atoms, phenyl and phenyl substituted with one or two methyl group, an aralkyl group, an alkoxyalkyl group or an alicyclic hydrocarbon group, and n is an integer of 1 to 3 for conversion of substantially all the carboxylic anhydride (A) into the monoester thereof to obtain a reaction mixture containing said monoester, 3,4,5,6-tetrahydrophthalic anhydride, and if any, a monoester of 3,4,5,6-tetrahydrophthalic anhydride, and
   (ii) adding ammonia to the reaction mixture obtained in the step (i) to subject the 3,4,5,6-tetrahydrophthalic anhydride, and if any, the monoester thereof to a reaction for conversion into 3,4,5,6-tetrahydrophthalimide, wherein the step (i) and step (ii) are conducted in the presence of at least one solvent selected from the group consisting of aliphatic hydrocarbons, alicyclic hydrocarbons and aromatic hydrocarbons each having 6 to 16 carbon atoms, or the step (ii) is conducted using as solvent as least one hydrocarbon selected from the group consisting of aliphatic hydrocarbons, alicyclic hydrocarbons and aromatic hydrocarbons all having 6 to 16 carbon atoms.

2. A process according to claim 1 wherein the crude 3,4,5,6-tetrahydrophthalic anhydride contains about 1 to about 20% by weight of the carboxylic anhydride (A) as impurities.

3. A process according to claim 1 wherein the crude 3,4,5,6-tetrahydrophthalic anhydride contains about 3 to about 15% by weight of the carboxylic anhydride (A) as impurities.

4. A process according to claim 1 wherein the alcohol of the formula (I) is a straight- or branched-chain aliphatic saturated or unsaturated alcohol having 1 to 22 carbon atoms; an adduct of such alcohol with a $C_2$–$C_3$ alkylene oxide; benzyl alcohol; phenethyl alcohol; cyclohexyl alcohol; decahydronaphthol; ethylene glycol; propylene glycol; glycerine; or an adduct of ethylene glycol, propylene glycol or glycerine with a $C_2$–$C_3$ alkyylene oxide.

5. A process according to claim 4 wherein the alcohol of the formula (I) is a straight- or branched-chain aliphatic saturated or unsaturated alcohol having 1 to 22 carbon atoms, benzyl alcohol, cyclohexyl alcohol, ethylene glycol, glycerin or propylene glycol.

6. A process according to claim 4 wherein the alcohol of the formula (I) is one having a boiling point of about 120° C. or higher.

7. A process according to claim 1 wherein the alcohol of the formula (I) is used in an amount of about 0.1 to about 20 moles per mole of the crude 3,4,5,6-tetrahydrophthalic anhydride in terms of the mean molecular weight as calculated from the neutralization value.

8. A process according to claim 1 wherein the alcohol of the formula (I) is used in an amount of about 0.5 to about 10 moles per mole of the crude 3,4,5,6-tetrahydrophthalic anhydride in terms of the mean molecular weight as calculated from the neutralization value.

9. A process according to claim 1 wherein the monoesterification reaction in the step (i) is conducted at a temperature of about 60° to about 140° C.

10. A process according to claim 1 wherein the hydrocarbon has a boiling point of about 140° C. or higher.

11. A process according to claim 1 wherein the solvent to be used in the step (ii) is dodecane, decalin or paraffin-naphthene hydrocarbon mixture having a boiling point of about 140° to about 255° C.

12. A process according to claim 1 wherein the combined amount of the hydrocarbon and the alcohol of the formula (I) is 25 to 250 wt. % based on the amount of the crude 3,4,5,6tetrahydrophthalic anhydride.

13. A process according to claim 1 wherein in the reaction of the step (ii), an aqueous ammonia solution is added to the reaction mixture obtained in the step (i).

14. A process according to claim 15 wherein the aqueous ammonia solution has a concentration of about 10 to about 35% by weight.

15. A process according to claim 15 wherein the aqueous ammonia solution has a concentration of about 20 to about 30% by weight.

16. A process according to claim 1 wherein the ammonia is used in an amount of about 1.01 to about 2.5 moles per mole of the crude 3,4,5,6-tetrahydrophthalic anhydride in terms of the mean molecular weight as calculated from the neutralization value.

17. A process according to claim 1 wherein the ammonia is gradually added in the step (ii).

18. A process according to claim wherein the reaction in the step (ii) is conducted at a temperature of about 100° to about 160° C.

19. A process according to claim 1 wherein the reaction in the step (ii) is conducted at a temperature of about 120° to about 140° C.

* * * * *